United States Patent [19]

Liu

[11] Patent Number: 5,309,338
[45] Date of Patent: May 3, 1994

[54] ROTATABLE LIGHTING EQUIPMENT

[76] Inventor: Zuo H. Liu, No. 61, Sec. 2, Tung Hsing Rd., Taichung, Taiwan

[21] Appl. No.: 968,489

[22] Filed: Oct. 29, 1992

[51] Int. Cl.[5] .............................................. F21V 33/00
[52] U.S. Cl. .................................... 362/253; 362/311; 362/269; 362/458; 362/812; 362/35; 40/431; 40/423
[58] Field of Search ............... 362/253, 812, 457, 458, 362/362, 326, 269, 311, 35; 40/409, 430–432, 435–438, 440

[56] References Cited

U.S. PATENT DOCUMENTS

| 1,814,995 | 7/1931 | Winer et al. | 40/431 |
| 1,937,138 | 11/1933 | Barclay | 40/432 |
| 3,247,609 | 4/1966 | Hayes et al. | 40/431 |
| 3,510,228 | 5/1970 | May | 362/253 X |
| 3,755,664 | 8/1973 | Reiback | 40/433 |
| 5,003,444 | 3/1991 | Secka et al. | 362/35 X |

FOREIGN PATENT DOCUMENTS 1228389  3/1960  France ................................ 362/35

Primary Examiner—Larry Jones
Attorney, Agent, or Firm—Peterson, Wicks, Nemer & Kamrath

[57] ABSTRACT

A lighting device includes a housing disposed on a base for accommodating perfume having a fragrance, a casing disposed on the housing for accommodating an electric fan in order to circulate the fragrance of the perfume from the housing toward the casing and outward of the casing, a motor and gear disposed on the casing, a cover disposed on the casing, and a light bulb disposed in the cover. The cover is rotated by the motor.

10 Claims, 2 Drawing Sheets

ROTATABLE LIGHTING EQUIPMENT

BACKGROUND OF THE INVENTION

1. Field of the Invention

The present invention relates to lighting equipment, and more particularly to rotatable lighting equipment.

2. Description of the Prior Art

Typically, lighting equipment for household usages is stably disposed in place and is not rotatable.

The present invention has arisen to provide novel lighting equipment.

SUMMARY OF THE INVENTION

The primary objective of the present invention is to provide rotatable lighting equipment including a housing rotatably provided therein.

In accordance with one aspect of the invention, there is provided lighting equipment comprising a base, a housing disposed on the base for accommodating perfume having a fragrance and including a plurality of holes formed therein, a casing disposed on the housing and including a plurality of orifices formed therein and including a projection radially extended inward from a lower portion thereof and including an annular groove formed in an upper and outer peripheral portion thereof, an electric fan fixed to the projection for circulating air from the housing toward the casing and outward of the casing, a socket and a motor disposed on an upper portion of the casing, a gear coupled to the motor and driven by the motor, a disc disposed above the casing and fixed to the casing, a light bulb plugged to the socket, and a cover including a lower end rotatably engaged in the annular groove of the casing and including an annular track formed in an inner and lower peripheral portion thereof for engagement with the gear of the motor, whereby, the cover is rotated by the motor by the engagement between the gear and the annular track of the cover, and the fragrance of the fragrance is circulated by the electric fan.

Further objectives and advantages of the present invention will become apparent from a careful reading of the detailed description provided hereinbelow, with appropriate reference to the accompanying drawings.

DETAILED DESCRIPTION OF THE PREFERRED EMBODIMENT

Figure 3:
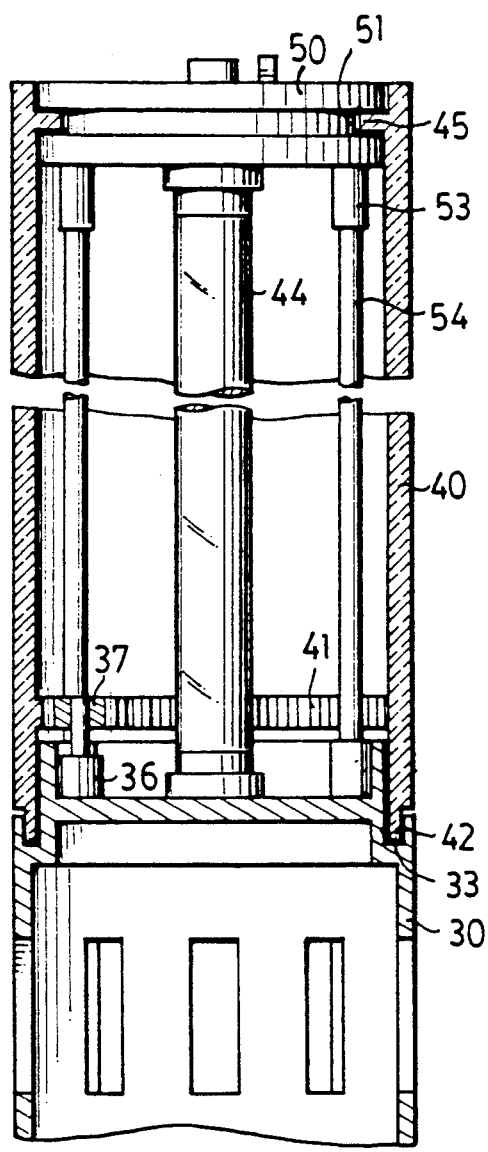
FIG. 3 is a cross sectional view taken along lines 3—3 of FIG. 1.
Figure 1:
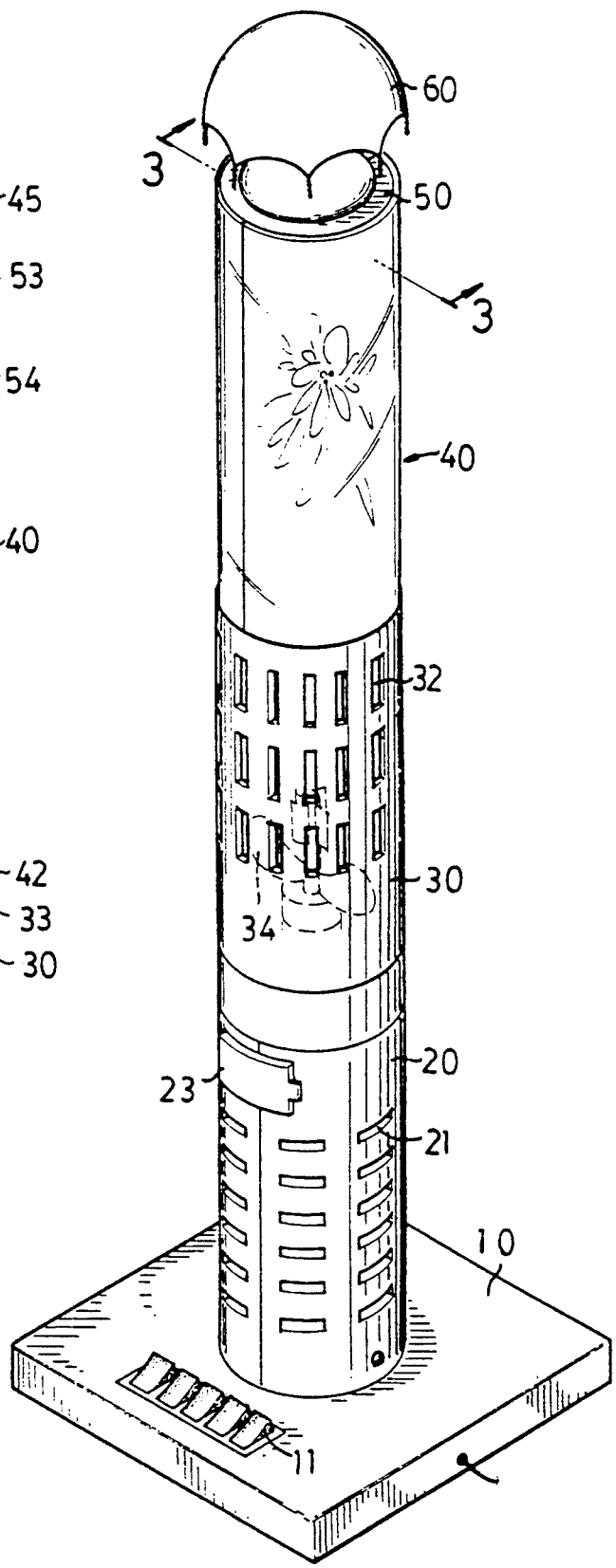
FIG. 1 is a perspective view of rotatable lighting equipment in accordance with the present invention.
Figure 2:
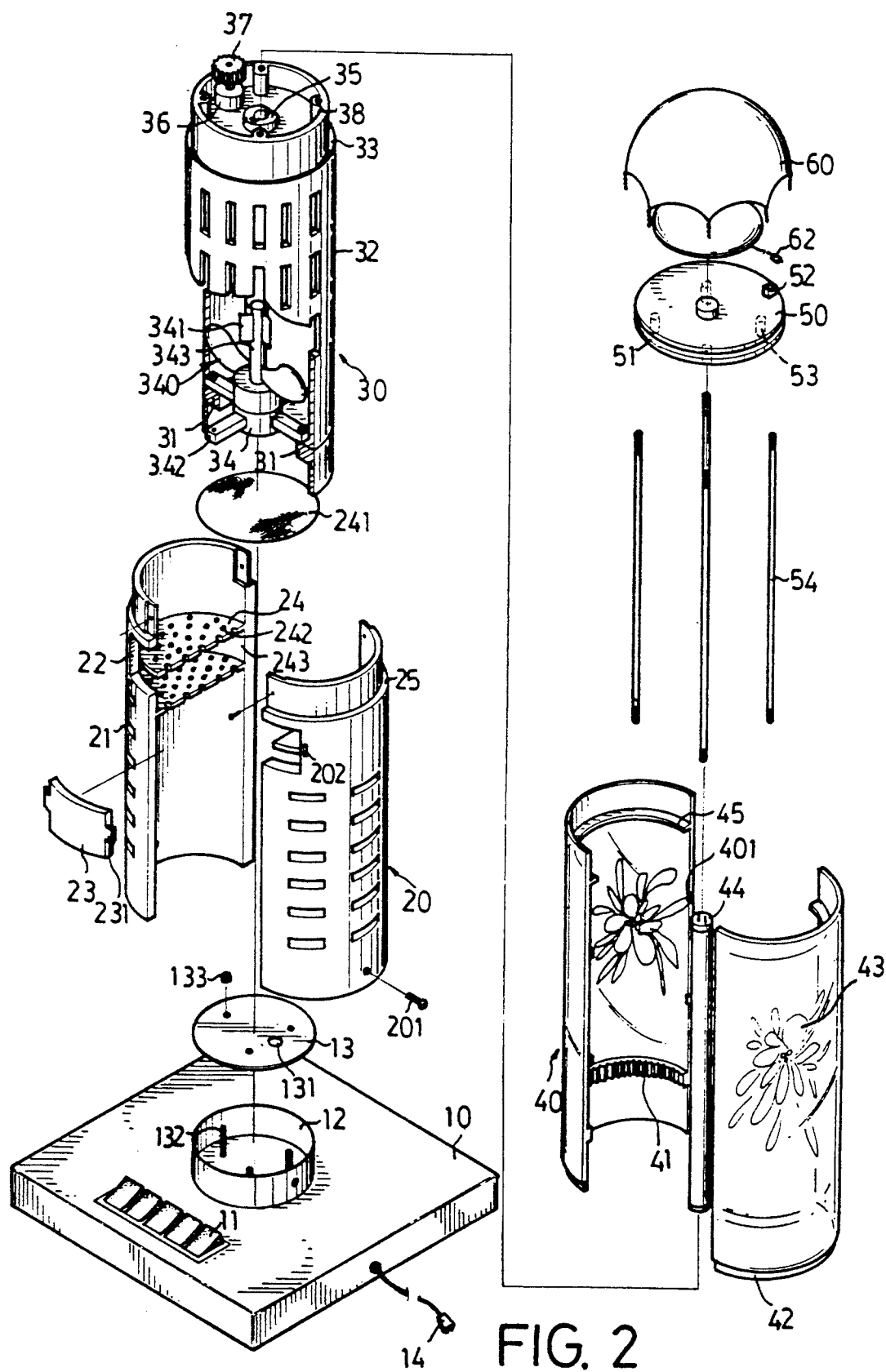
FIG. 2 is an exploded view of the rotatable lighting equipment.

Referring to the drawings, rotatable lighting equipment in accordance with the present invention comprises a base 10 including a plurality of switch buttons 11 disposed thereon for controlling the operations of the lighting equipment. A cylindrical wall member 12 extends upward from the base 10 and is enclosed by a cap 13 which includes a hole 131 formed therein and which is supported in place by bolts 132 and nuts 133 such that a space is formed within the wall member 12 for accommodating electric wires. Electric wires may extend through the hole 131 of the cap 13. The base 10 includes a plug 14 connected thereto for coupling to an electric source.

A housing 20 has a lower end engaged on the wall member 12 and fixed to the wall member 12 by screws 201. The housing 20 is cylindrically shaped and includes two halves having a plurality of holes 21 formed therein. The housing 20 includes an opening 22 formed therein and enclosed by a lid 23 which includes a pair of lugs 231 oppositely extended outward therefrom. A protrusion (not shown) is formed on each of the lugs 231 for engagement in the holes 202 of the housing 20 so that the lid 23 can be attached to the housing 20 for enclosing the opening 22. Two discs 24 are formed integral in the upper portion of the housing 20 and are arranged in parallel such that a space 243 is formed between the discs 24 for accommodating a package of perfume 241 and the like. Each of the discs 24 have a plurality of apertures 242 formed therein such that the fragrance of the perfume 241 may permeate through the apertures 242. An an annular shoulder 25 is formed in the outer peripheral portion of the housing 20. The package of perfume 241 may be disposed into the space 243 via the opening 22.

A casing 30 includes a lower end force-fitted onto the housing 20 and engaged with the annular shoulder 25 of the housing 20. Two or more projections 31 extend radially inwards of the casing 30 from the lower portion thereof. A plurality of orifices 32 are formed in the casing 30. An annular groove 33 is formed in the upper portion of the outer peripheral portion of the casing 30. A support 34 includes two or more bars 342 extending outward therefrom in order to be fixed on the projections 31. An electric fan 340 is disposed on the support 34 and includes a motor and two fan blades and includes a set of smaller fan blades 341 fixed on the spindle 343 of the motor. The electric fan 340 is provided for pumping air upward from the housing 20 toward the casing 30 in order to circulate the fragrance of the perfume 241. A socket 35 and a motor 36 are disposed on the upper portion of the casing 30. The motor 36 includes a gear 37 fixed to the spindle thereof such that the gear 37 can be driven by the motor 36. Four screw holes 38 are formed in the upper portion of the casing 30.

A cover 40 which is preferably made of glass materials includes two halves coupled together by the protrusions 401 formed on one half and the corresponding depressions (not shown) formed in the other half. The cover 40 includes an annular flange 42 formed in the bottom portion thereof and rotatably engaged in the annular groove 33 of the casing 30. An annular track 41 is formed in the inner peripheral portion thereof for engagement with the gear 37 such that the cover 40 can be rotated by the motor 36. A color pattern 43 is formed in the cover 40, a light bulb 44 is disposed in the cover 40 and has one end engaged in the socket 35 of the casing 30. An annular rib 45 is formed in the inner and upper portion of the cover 40.

A disc 50 includes an annular recess 51 formed in the outer peripheral portion thereof and four stubs 53 extending downward from the lower portion of the disc 50, with each stub 53 having a screw hole formed therein. Four bolts 54 each have an upper end engaged in the screw holes of the stubs 53 and have a lower end engaged in the screw holes 38 of the casing 30 so as to support the disc 50 in place. The annular rib 45 of the cover 40 is rotatably engaged in the annular recess 51 of the disc 50. A socket 52 is provided on the upper portion of the disc 50. An artistic lamp 60 may further be disposed on the disc 50 and includes a plug 62 for plugging into the socket 52.

In operation, the fragrance of the perfume 241 may be circulated by the electric fan 340, the glass cover 40 can be rotated by the motor 36, and the artistic lamp 60 may further be disposed upon the disc 50 such that the rotatable lighting equipment is suitable for household usages.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. Lighting equipment comprising a casing including an annular groove formed in an upper and outer peripheral portion thereof, a socket and a motor disposed on an upper portion of said casing, a gear coupled to said motor and driven by said motor, a first disc disposed above said casing and fixed to said casing, wherein said first disc includes an annular recess formed in an outer peripheral portion thereof, a light bulb plugged into said socket, and a cover including a lower end rotatably engaged in said annular groove of said casing and including an annular track formed in an inner and lower peripheral portion thereof for engagement with said gear of said motor, wherein said cover includes an annular rib formed in an inner and upper peripheral portion thereof for rotatably engaging in said annular recess of said first disc, whereby said cover is rotated by said motor by the engagement between said gear and said annular track of said cover.

2. The lighting equipment according to claim 1 further comprising an artistic lamp disposed above said first disc.

3. Lighting equipment comprising a casing including an annular groove formed in an upper and outer peripheral portion thereof, a socket and a motor disposed on an upper portion of said casing, a gear coupled to said motor and driven by said motor, a first disc disposed above said casing and fixed to said casing, a light bulb plugged into said socket, a cover including a lower end rotatably engaged in said annular groove of said casing and including an annular track formed in an inner and lower peripheral portion thereof for engagement with said gear of said motor, whereby said cover is rotated by said motor by the engagement between said gear and said annular track of said cover, a base, a housing disposed on said base for accommodating a perfume having a fragrance and including a plurality of holes formed therein, said casing being disposed on said housing and including a plurality of orifices formed therein and including a projection radially extended inward from a lower portion thereof, and an electric fan fixed to said projection for circulating air from said housing toward said casing and outward of said casing, whereby, the fragrance of said perfume is circulated by said electric fan.

4. The lighting equipment according to claim 3, wherein said housing includes two second discs formed in parallel in an upper portion thereof so as to form a space therebetween for accommodating said fragrant, and each of said second discs includes a plurality of apertures formed therein for permeating of said fragrant.

5. The lighting equipment according to claim 4, wherein said housing includes an opening formed therein and communicated with said space formed between said second discs for insertion of said fragrant.

6. The lighting equipment according to claim 3 further comprising an artistic lamp disposed above said first disc.

7. Lighting equipment comprising a base, a housing disposed on said base for accommodating fragrant and including a plurality of holes formed therein, a casing disposed on said housing and including a plurality of orifice formed therein and including a projection radially extended inward from a lower portion thereof and including an annular groove formed in an upper and outer peripheral portion thereof, an electric fan fixed to said projection for circulating air from said housing toward said casing and outward of said casing, a socket and a motor disposed on an upper portion of said casing, a gear coupled to said motor and driven by said motor, a first disc disposed above said casing and fixed to said casing, a light bulb plugged to said socket, and a cover including a lower end rotatably engaged in said annular groove of said casing and including an annular track formed in an inner and lower peripheral portion thereof for engagement with said gear of said motor, whereby, said cover is rotated by said motor by the engagement between said gear and said annular track of said cover, and the perfume of said fragrant is circulated by said electric fan.

8. The lighting equipment according to claim 7, wherein said first disc includes an annular recess formed in an outer peripheral portion thereof, said cover includes an annular rib formed in an inner and upper peripheral portion thereof for rotatably engaging in said annular recess of said first disc.

9. The lighting equipment according to claim 7, wherein said housing includes two second discs formed in parallel in an upper portion thereof so as to form a space therebetween for accommodating said fragrant, and each of said second discs includes a plurality of apertures formed therein for permeating of said fragrant.

10. The lighting equipment according to claim 9, wherein said housing includes an opening formed therein and communicated with said space formed between said second discs for insertion of said fragrant.

* * * * *